United States Patent [19]

Takahashi et al.

[11] Patent Number: 4,818,935
[45] Date of Patent: Apr. 4, 1989

[54] METHOD AND APPARATUS FOR NON-DESTRUCTIVELY DETECTING DEFECTS IN METAL MATERIALS BY USING ROTATING MAGNETIC FIELDS GENERATED BY MULTIPHASE AC CURRENT

[75] Inventors: Michiaki Takahashi; Mitsuo Yoshida; Kazuyoshi Miyazawa; Sigeyuki Nitta; Junichi Fujisawa, all of Muroran; Nobuji Obara, Sapporo; Shoji Hayashibe, Iruma; Yoshikazu Sawada, Kawaguchi, all of Japan

[73] Assignees: Nippon Steel Corporation; Eddio Corporation, both of Tokyo, Japan

[21] Appl. No.: 26,793
[22] PCT Filed: Jul. 2, 1986
[86] PCT No.: PCT/JP86/00340
§ 371 Date: Feb. 5, 1987
§ 102(e) Date: Feb. 5, 1987
[87] PCT Pub. No.: WO87/00287
PCT Pub. Date: Jan. 15, 1987

[30] Foreign Application Priority Data

Jul. 3, 1985 [JP] Japan ................ 60-146166
Nov. 22, 1985 [JP] Japan ................ 60-263452
Jan. 24, 1986 [JP] Japan ................ 61-13442

[51] Int. Cl.$^4$ ................ G02N 27/72; G02N 27/82; G01R 33/12
[52] U.S. Cl. ................ 213/232; 324/233; 324/242
[58] Field of Search ........... 324/232, 227, 238–243, 324/233

[56] References Cited

U.S. PATENT DOCUMENTS 2,448,794 9/1948 Goldsmith, Jr. et al. ......... 324/232
3,944,911 3/1976 Tornblom ....................... 324/242
3,971,981 7/1976 Tornblom ....................... 324/225

FOREIGN PATENT DOCUMENTS 0048361 3/1982 European Pat. Off. .

Primary Examiner—Reinhard J. Eisenzopf
Assistant Examiner—Walter E. Snow
Attorney, Agent, or Firm—Pollock, Vande Sande & Priddy

[57] ABSTRACT

Method and apparatus for non-destructive inspection of flaws in metal materials include exciting coils centered on a longitudinal axis of a cylindrical or columnar metallic material to be examined being arranged to surround the examinee material. A multiphase alternating current of such a relatively low frequency as to cause the exciting coils to generate a rotating magnetic field which rotates about the longitudinal axis of the examinee material is superimposed with a high frequency alternating current having an inspection frequency selected on the basis of the necessary sensitivity for detection of surface flaws of the examinee material. The composite multiphase current is applied to the exciting coils so that an electromagnetic effect induced in the surface of the examinee material by the high frequency alternating current is rotated for shifting circumferentially about the examinee material along with the rotating magnetic field. A detecting element group disposed in the proximity of the surface of the examined material detects the changing of the electromagnetic effect, dependent on the presence or absence of a surface flaw of the examinee material.

8 Claims, 9 Drawing Sheets

METHOD AND APPARATUS FOR NON-DESTRUCTIVELY DETECTING DEFECTS IN METAL MATERIALS BY USING ROTATING MAGNETIC FIELDS GENERATED BY MULTIPHASE AC CURRENT

TECHNICAL FIELD

This invention relates to a method and apparatus for detection of defects in steel materials by using a rotating magnetic field and more particularly to a method and apparatus for the non-destructve inspection of flaws in a to be examined cylindrical or columnar metallic material by applying a rotating magnetic field which rotates around the outer circumferential surface of the to be examined material or examinee material.

BACKGROUND ART

Known as a method for non-destructive inspection of surface flaws or crack flaws in a cylindrical or columnar metallic material such as, for example, a steel bar or a steel pipe is an eddy current inspection method wherein a high frequency magnetic field of several KHz to several of tens of KHz is applied to a material to be examined so that the state of an eddy current generated in the surface of the examinee material is changed dependent on the presence or absence of a flaw; followed by a change in magnetic flux generated by the eddy current, and the change is detected by a detecting element such as a detection coil disposed in the proximity of the examinee material. In the case of the material to be examined being non-magnetic, a magnetic inspection method is known wherein a detecting element such as a Hall element or a detection coil disposed in the proximity of the material to be examined detects that the state of leakage magnetic flux generated at the surface of the examinee material by a high frequency magnetic field mentioned as above is changed dependent on the presence or absence of a flaw. Principles of these detection methods are disclosed in detail in "Industrial Instrumentation Handbook" published by Asakura Shoten, March, 1982, pp. 633–641.

When inspecting the entire circumference of the material to be examined in accordance with any of the above inspection methods, it is necessary to rotate the material to be examined while an inspection apparatus, comprised of an exciter for application of the magnetic field and the detecting element, is kept stationary; or it is necessary to rotate the inspection apparatus around the material to be examined while the examinee material is kept stationary. In either case, a rotation mechanism is required, therefore, increasing the overall size of the apparatus. Furthermore, the inspection is time-consuming. To solve these problems, a method is proposed in the specification of British Pat. No. 1,436,186, according to which a cylindrical exciter of a multiphase alternating current winding structure such as a stator of an induction motor is provided. A multiphase alternating current is passed through the exciter to generate a rotating magnetic field; and surface flaws of a material to be examined, which is inserted for passage through the exciter, are detected by a toroidal coil disposed in the proximity of the surface of the examinee material and surrounding the same. In this method, however, the multiphase alternating current to be passed through the exciter is of a single frequency as described in the aforementioned British Patent Specification; and this method is suitable for use with a low frequency. But if use with a high frequency, the core of the exciter mut be removed; alternatively the core must be made of a special material such as ferrite. When the low frequency magnetic field is used, sensitivity is degraded, and especially sensitivity to surface flaws of the material to be examined is seriously degraded and the detection becomes almost impossible. Especially where the high frequency is used with the core made of such a material as ferrite, an attendant increase in the number of revolutions of the rotating magnetic field gives rise to an increase in noise, thus preventing the frequency from increasing to an extent that practically sufficient sensitivity can be obtained.

Accordingly, an object of this invention is to provide a method and apparatus for non-destructive inspection of flaws in metal materials which does not require relative mechanical rotation between a material to be examined and the inspection apparatus and which can exhibit sufficient sensitivity of detection of surface flaws of the material to be examined.

SUMMARY OF INVENTION

To accomplish the above object, according to the method and apparatus of the invention, exciting coils centered on a longitudinal axis of a cylindrical or columnar metallic material to be examined are arranged to surround the examinee material. A multiphase alternating current of such a relatively low frequency as to cause the exciting coils to generate a rotating magentic field which rotates about the longitudinal axis of the examinee material is superimposed with a high frequency alternating current, of an inspection frequency selected on the basis of necessary sensitivity for detection of surface flaws of the examinee material, and applied to the exciting coils so that an electromagnetic effect created at the surface of the examinee material by the high frequency alternating current is rotated for shifting circumferentially the examinee material along with the rotating magnetic field. And a detecting element group disposed in the proximity of the surface of the examinee material detects the electromagnetic effect changed by the presence of a surface flaw of the examinee material.

In a more preferable mode of the invention, respective phases of the low frequency multiphase alternating current for generation of the rotating field are independently balance-modulated with the high frequency alternating current and applied to the exciting coils.

BEST MODE FOR CARRYING OUT THE INVENTION

Figure 1:
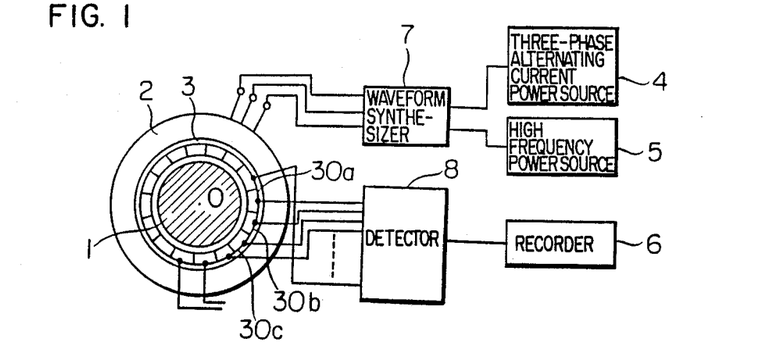
FIG. 1 is a block diagram showing the construction of a first embodiment of the invention.
Figure 2A:
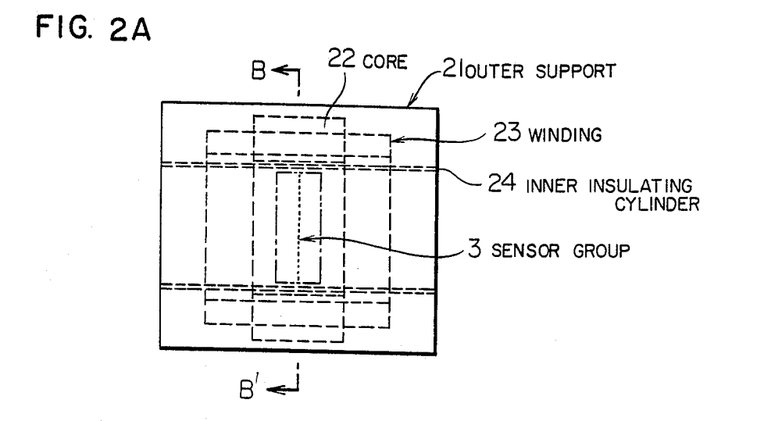
FIG. 2A is a side view of an exciter in the embodiment of FIG. 1.
Figure 2B:
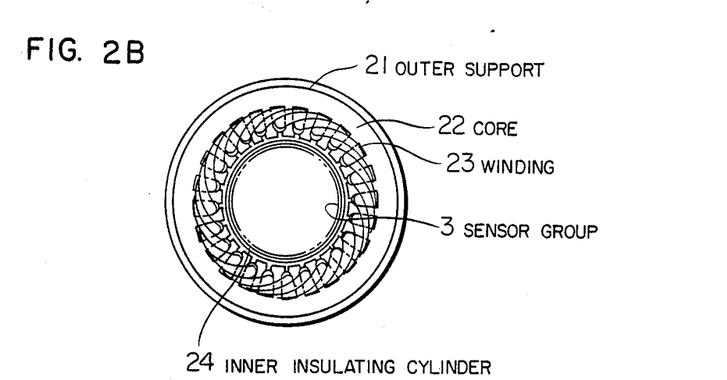
FIG. 2B is a sectional view taken along B-B' of FIG. 2A.

A first embodiment of the invention will be described with reference to FIG. 1. In FIG. 1, 1 designates a cylindrical or columnar metallic material to be examined. An exciting unit 2 for generating a rotating magnetic field which rotates about a longitudinal axis 0 of the material 1 to be examined is so disposed as to surround the examinee material 1, and a sensor group 3 is disposed between examinee material 1 and exciting unit 2 along the inner circumferential surface of the exciting unit 2. The exciting unit 2 has a similar construction to a stator of a multiphase induction motor and comprises, as shown in FIGS. 2A and 2B, a core 22 supported by a cylindrical outer support 21, a multiphase winding 23 fitted in slots formed in the inner circumferential surface of the core 22, and an inner insulating cylinder 24 disposed interiorly of the multiphase winding. For simplicity of explanation, when describing an instance using a three-phase alternating current the winding 23 comprises three coils which are spaced at intervals of an electrical angle of $2\pi/3$ and under excitation using a three-phase alternating current at a frequency fHz, a rotating magnetic field of a revolution number $R = 120f/P$ (rpm) is generated, where P is the number of poles.

Figure 3A:
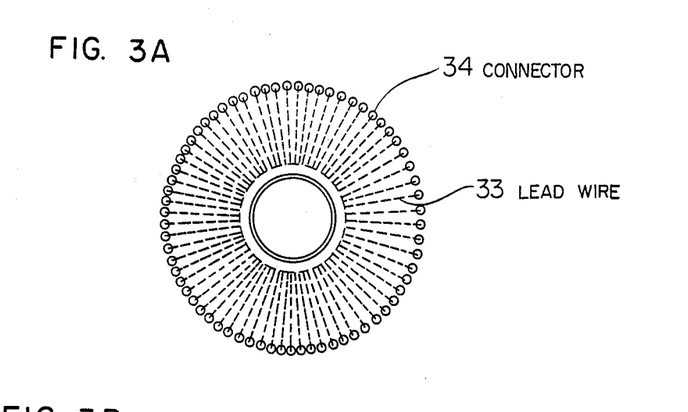
FIG. 3A and FIG. 3B are a front view and a side view respectively showing the construction of a sensor group.
Figure 3B:
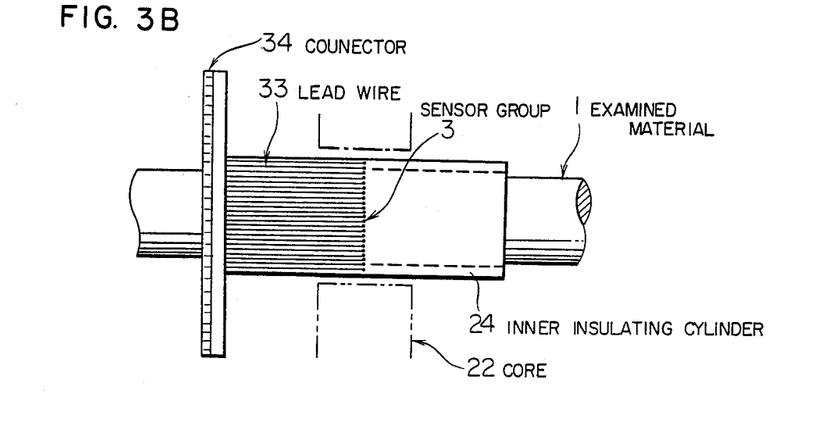
Figure 4A:
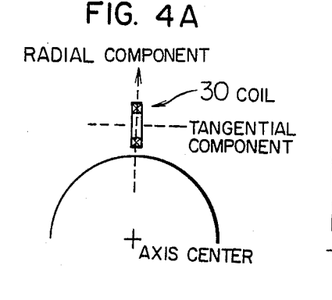
FIG. 4A and FIG. 4B are front and side views showing the disposition of a sensor coil.
Figure 4B:
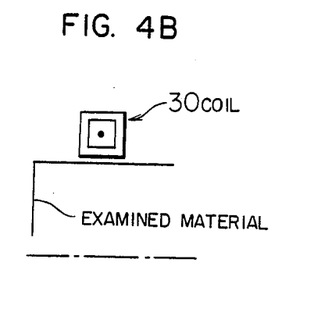

The sensor group 3 comprised of a number of sensors 30 is arranged in line in the circumferential direction along the inner wall of the inner insulating cylinder 24. As illustrated in detail in FIGS. 3A and 3B, each sensor 30 is connected to a connector 34 by a lead wire 33. A group of connectors 34 are arranged on a disc having a larger diameter than that of the insulating cylinder 24 to assure suffcient spacing between elements. For the sensor, a magnetic detecting element such as a Hall element, a magnetoresistive element or a detection coil may satisfactorily be used; and the direction of flux to be detected may be either radial or tangential with respect to the outer circumference of the examinee material. FIGS. 4A and 4B illustrate the posture of a coil when a tangential component of a magnetic field is detected by using a detection coil 30 as the sensor. When detecting a radial component, the coil as illustrated in FIG. 4A is rotated through 90° so that the coil surface may be directed tangentially. The smaller the detection coil, the higher the sensitivity becomes, and a detection coil of 6 to 8 mm diameter is typically used.

Figure 10:
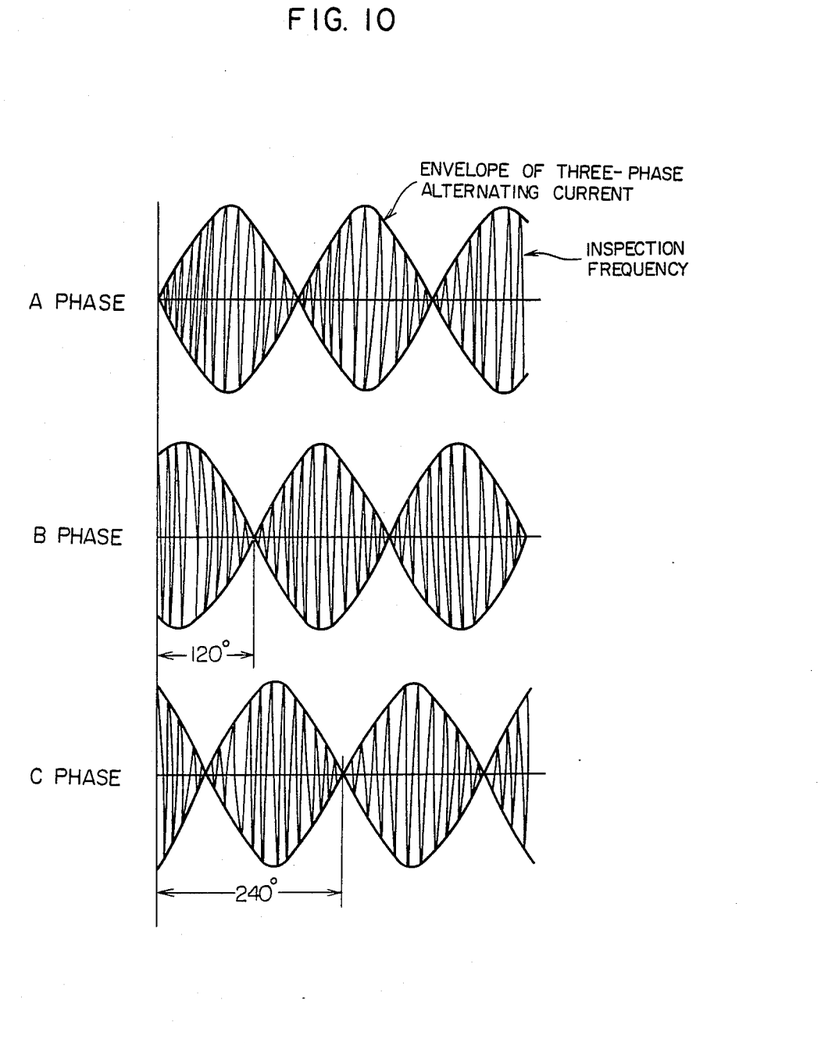
FIG. 10 is a diagram showing waveforms of a balance-modulated multiphase alternating current to be applied to an exciter in the second embodiment.

Returning to FIG. 1, the winding of sensor group 3 of the exciting unit 2 is applied with a composite current, which is obtained by synthesizing, by means of a waveform synthesizer 7, a three-phase alternating current generated from a three-phase alternating current power source 4, having a low frequency elected in accordance with a desired revolution number of the rotating magnetic field, and a high frequency alternating current generated from a high frequency power source 5, having a frequency suitably used as an inspection frequency. This composition may be effected in a manner of either addition or multiplication; and preferably, a composite wave as shown in FIG. 10 is used. The composite wave is obtained by balance-modulating the low frequency alternating current with the high frequency alternating current, as will be described later. Preferably, the frequency of the three-phase alternating current for generating the rotating magnetic field may be 1 to 1000 Hz when utilizing eddy currents and 1 to 900 Hz when utilizing leakage flux, and the inspection frequency may be 10 to 1000 KHz when utilizing eddy currents and 1 to 100 KHz when utilizing leakage flux.

The exciting unit 2 responds to the composite alternating current to generate a rotating magnetic field which rotates circumferentially about a cross section of the examinee material, i.e., about the longitudinal axis 0 at a rotating speed determined by the frequency of the low frequency alternating current. The sensor group 3 detects that an electromagnetic effect such as eddy current or leakage flux generated at the surface of the examinee material by the superimposed high frequency alternating current is changed dependent on the presence or absence of a surface flaw of the examinee material. Thus, respective sensors 30a, 30b, 30c are connected to a detector 8 whose output is recorded on a recorder 6. Since, in the presence of a surface flaw, the output of a sensor in association with the position of the surface flaw is changed, the presence and position of that flaw can be recognized from an output waveform recorded on the recorder 6. This will be explained by referring to FIG. 5.

Figure 5:
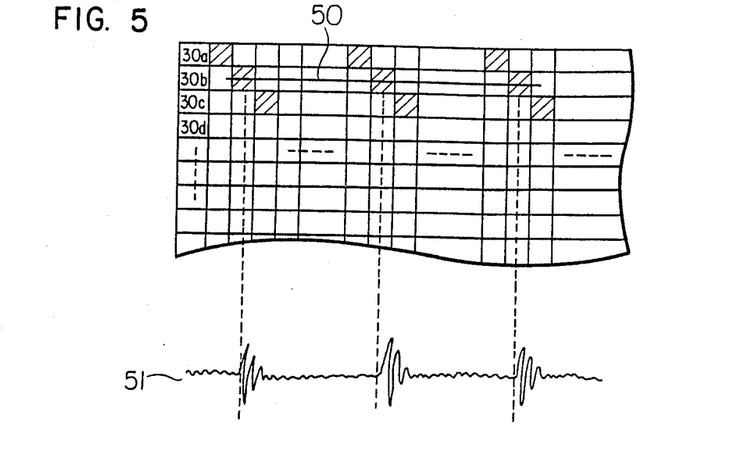
FIG. 5 is a diagram showing the relation between flaw position and detection signal.

Referring to FIG. 5, the ordinate represents the sensors 30a, 30b, 30c, ... arranged circumferentially about a cross section of the examinee material, the abscissa represents the longitudinal direction of the examinee material, and a hatched portion represents a sensor which detects an electromagnetic effect (eddy current or leakage flux) induced in the surface of the examinee material by the rotating magnetic field. Since the magnetic field generated by the exciting unit rotates at a predetermined period circumferentially about the cross section of the examinee material as described previously, the electromagnetic effect induced in the surface of the examinee material by this magnetic field becomes as if it were rotating circumferentially about the cross section of the examinee material; and accordingly, the position of a sensor which detects this electromagnetic effect shifts circumferentially about the cross section in synchronism with the roating speed of the magnetic field, as indicated at hatched portions in the same figure. Assuming now that a crack flaw 50 exists in the surface of the examinee material as shown in the same figure, a flaw signal is obtained as indicated at 51 each time a sensor directly above the crack flaw 50 is activated.

Figure 6:
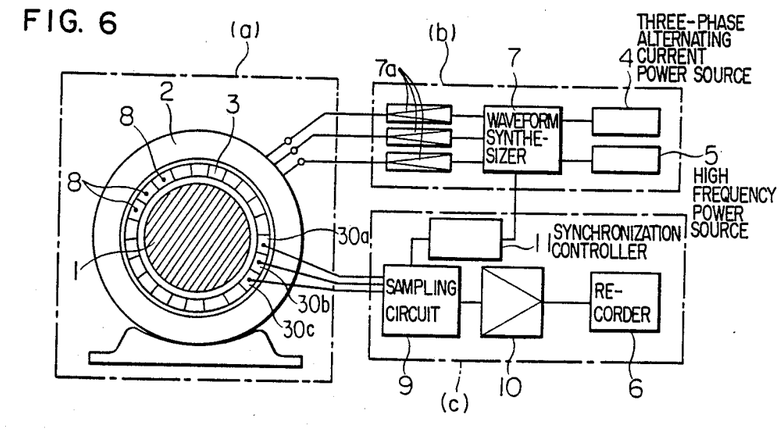
FIG. 6 is a block diagram showing a modification of the first embodiment.

A modification of the first embodiment will be described with reference to FIG. 6. In FIG. 6, components like those of FIG. 1 are designated by identical characters. A detecting portion (a) of FIG. 6 is the same as the corresponding portion of FIG. 1. A transmitting circuit (b) has amplifiers 7a which amplify respective phases of a composite current produced from the waveform synthesizer 7. A receiving circuit (c) resembles that of FIG. 1 by comprising the recorder 6 but has a sampling circuit 9, a differential amplifier 1 and a synchronization controller 11 which substitutes for the detector 8 of FIG. 1. The synchronization controller 11 outputs a pulse signal synchronous with the rotating frequency of the rotating magnetic field obtained from the waveform synthesizer 7. The sampling circuit 9 has a switch group (not shown) arranged in correspondence to individual sensors 30a, 30b, . . . of the sensor group 3 and is opreable to connect an output of each sensor to the differential amplifier 10 through a corresponding switch, the individual switches being sequentially closed by the pulse signal from the synchronization controller 11 to sequentially sample the individual sensor outputs. Since an electromagnetic effect, for example, leakage flux induced at the surface of the examinee material by the rotating magnetic field also shifts circumferentially about the surface of the examinee material in synchronism with the rotating magnetic field, the phase of the pulse signal from the synchronization controller 11 is adjusted to ensure that a switch connected to a sensor at a position corresponding to the shifting leakage flux can be closed. This phase adjustment is carried out by providing a phase adjuster (not shown) in the synchronization controller 11 and by adjusting the phase of the pulse signal by means of the phase shifter in such a manner that when the apparatus is operated with a material to be examined, which has a small flaw corresponding to a single detection coil scratched at a previously known location, inserted in the detecting portion (a), the output of the differential amplifier 10 becomes maximum. The differential amplifier 10 in receipt of the sensor output amplifies an output of a level in excess of a predetermined reference level and applies an amplified output to the recorder 6.

A second embodiment of the invention will now be described with reference to FIG. 7. A detecting portion 70 is the same as that of FIG. 1. A transmitting circuit 71 comprises a two-phase alternating current generator 72 for generating a two-phase alternating current of a low frequency determined in accordance with a revolution number of the rotating magnetic field, and phase shifter circuits 72a and 72b for respective 240° and 120° phase shiftings of the output of the generator 72. The outputs of the 240° and 120° phase shifter circuits 72a and 72b and of the two-phase alternating current generator 72 are respectively applied to balanced modulators 73a, 73b and 73c so as to balance-modulate a high frequency alternating current of several KHz to several of tens of KHz generated from an inspection frequency generator 80, thereby producing a three-phase alternating current of A phase, B phase and C phase. This three-phase alternating current is amplified by amplifiers 74a, 74b and 74c and applied to the three-phase winding of the detecting portion so that a rotating magnetic field superimposed with the high frequency alternating current of the high inspection frequency can be obtained.

A sensor group 30 is constructed similarly to that of the first embodiment, wherein each of the sensors 30a, 30b, . . . 30n has one end grounded and the other end connected to a respective phase detector 76a, 76b, . . . or 76n through a corresponding amplifier 75a, 75b, . . . or 75n. Each phase detector phase-detects an inputted sensor output by using as a reference wave the output of inspection frequency generator 80 which is phase-shifted through a phase shifter circuit 79 and generates a phase-detected output.

In the absence of a material to be examined, the output voltage of each sensor is zero because no magnetic flux interlinks the coil. When a material to be examined whose circumferential surface is devoid of flaw and uniform is inserted, each sensor detects a uniform eddy current reaction signal but this signal, can be cancelled out by suitably setting the reference wave phase of phase detection, and can be prevented from developing in the phase detector. The phase shifter circuit 79 is phase-adjusted such that the output of the phase detector becomes zero when the examinee material has no flaw.

Figure 11:
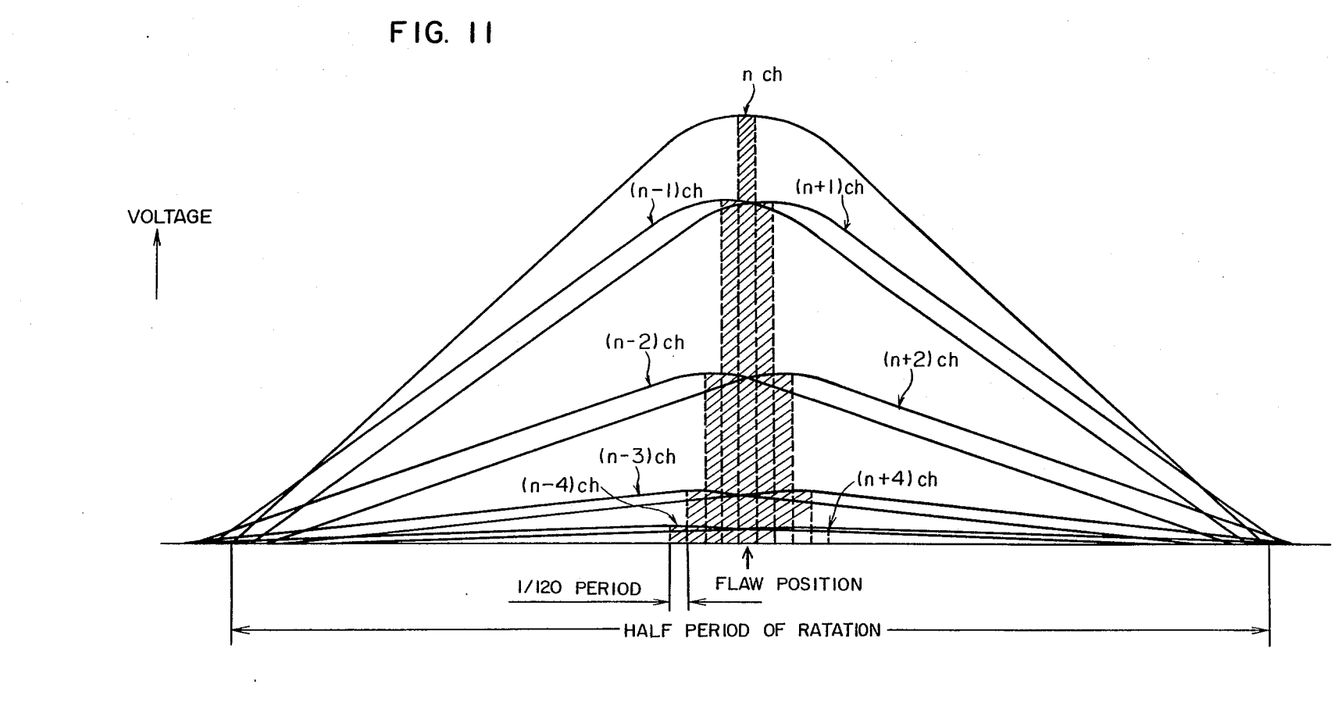
FIG. 11 is a diagram showing output waveforms of sensors.

With an examinee material has a flaw, the eddy current is locally disturbed and a sensor near that flaw produces an induced voltage which is different from that produced from another sensor in phase and amplitude. The induced voltage changes as the magnetic field rotates. Consequently, the phase-detected output originating from the induced voltage of that coil becomes a sine wave having the same period as that of the rotating magnetic field. And the amplitude of the output from a sensor most proximate to the flaw becomes maximum and the amplitude of the sensor output becomes smaller in proportion to deviation from the flaw position. This condition is illustrated in FIG. 11. In this figure, assuming that a sensor nch is situated directly above a flaw, (n−1)ch represents a coil next to the coil nch to the left, (n+1)ch reprsents a coil next to the coil nch to the right, (n−2)ch represents a coil next to the (n−1)ch to the left, (n+2)ch represents a coil next to the (n+1)ch to the right and so on. These waveforms correspond to the phase detector outputs which are passed through low-pass filters 77a, 77b, . . . 77n so as to be removed of the inspection frequency component.

Outputs from the low-pass filters are sent to a band-pass filter 84 through electronic switches 78a, 78b, . . . 78n. Each of the switches 78a, 78b, . . . is constituted by, for example, a field effect transistor and opened or closed by an output from a ring counter 83. One phase of the three-phase alternating current for generating the rotating magnetic field is inputted to a phase shifter circuit 81, which phase-shifts the current to a desired phase within a range of from 0° to 360°. The current is then inputted to a frequency multiplier 82 of phase-locked type. Assuming that the number of the sensors 30a, 30b, . . . is n, the frequency multiplier 82 performs n multiplication and, accordingly, given the frequency of the three-phase alternating current being f, it outputs nf which in turn is supplied to an n-step (n-nary) ring counter 83. The ring counter 83 has n switch control outputs and hence each of the switches 78a, 78b, . . . is rendered on once during one period of the three-phase alternating current. The phase of the output from the phase shifter circuit 81 is so adjusted as to ensure that the output of the ring counter 83 can close a switch connected to a sensor situated at a position opposing a shifting eddy current generated in the surface of the examinee material by the rotating magnetic field. Each switch remains on during an interval of time equal to 1/n of the period of the three-phase alternating current, n being 120, for example. In this manner, the outputs of the individual sensors are sequentially sampled. In the absence of the examinee material, the outputs of the low-pass filters 77a, 77b . . . are zero and the outputs sampled by the switches 78a, 78b, . . . are also zero. Where the material to be examined having no flaw is inserted for loading, owing to eccentricity in the insertion as well as rotationally asymmetric shape and unevenness in quality of the material, there occurs an output of a relatively small amplitude having a period which is equal to or about half the period of the rotating magnetic field. The outputs sampled by the switches 78a, 78b, . . . are sent to the band-pass filter 84 where they are removed of signals other than the flaw information, that is, a gradually varying signal due to the uneven quality and a spite signal attendant on switching.

The output of the ring counter 83 is fedback to the frequency multiplier 82 so that the final stage output pulse of the counter may be locked to a reference phase of the sinusoidal output from the phase shifter circuit 81, for example, a phase of zero-cross point.

The relation of the position of the rotating magnetic field relative to the sampling timing for the sensor output can be changed by effecting the phase shift by means of the phase shifter circuit 81, and it is possible to sample a sensor output at a position where a maximum flux density portion of the rotating magnetic field is operating or to sample a detection coil output at a position where a zero flux density portion is operating.

Figure 7:
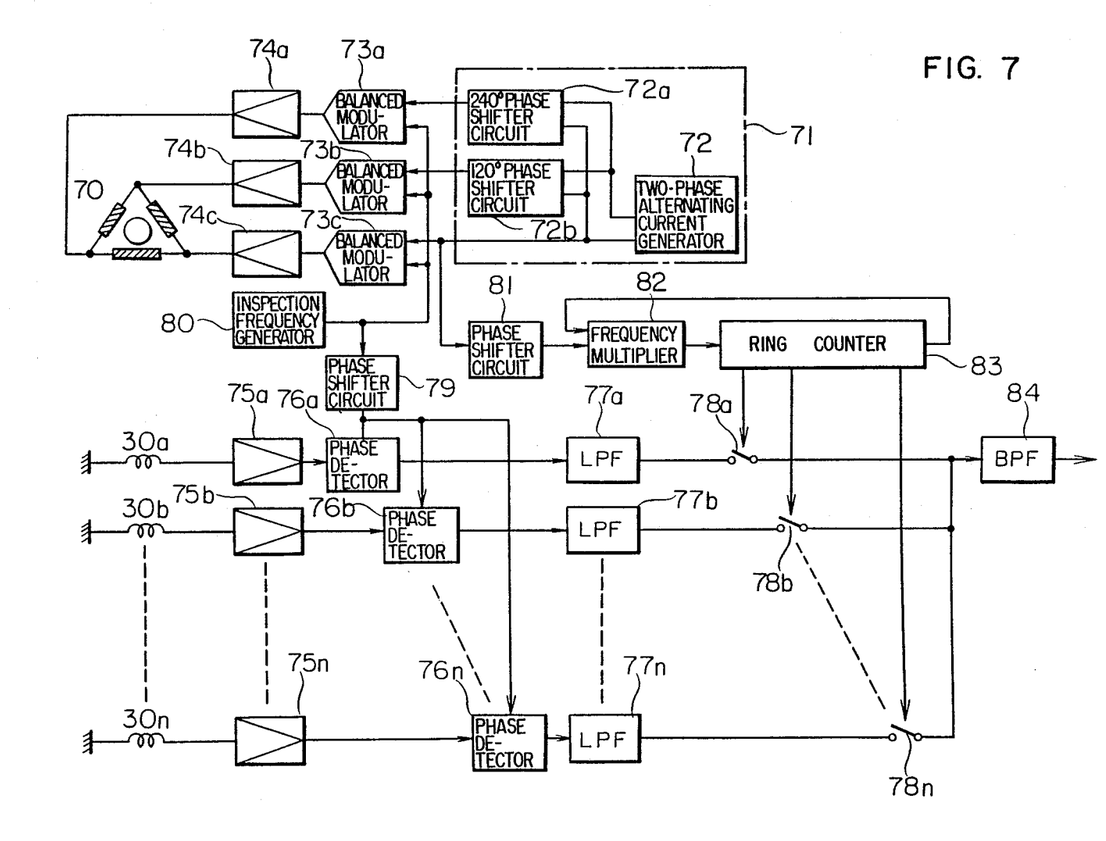
FIG. 7, FIG. 8 and FIG. 9 are block diagrams showing various modifications of a second embodiment of the invention.
Figure 8:
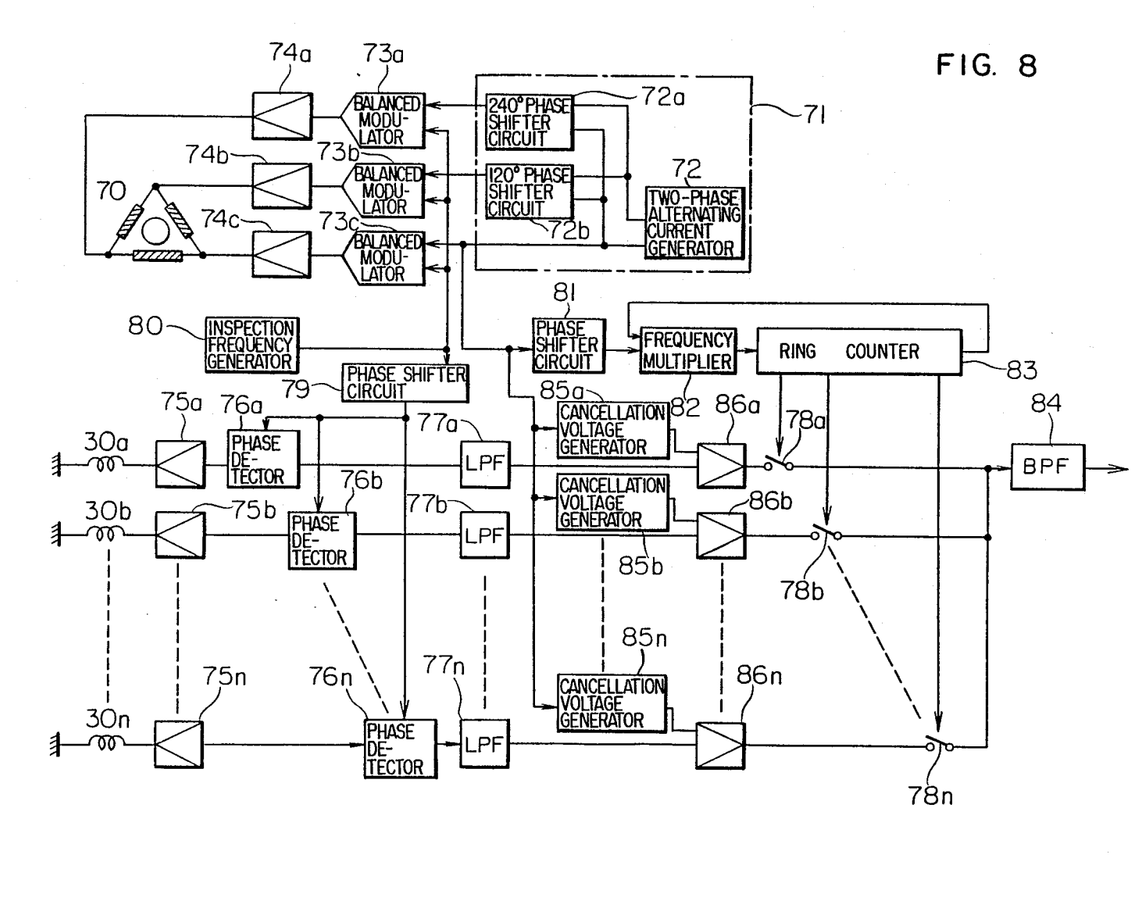

FIG. 8 shows addition to FIG. 7 of cancellation voltage generator 85a, 85b, . . . and differential amplifiers 86a, 86b, . . . . These components function to cancel out inherent outputs to the set (noises) due to irregularity in magnetic pole and winding of the rotating magnetic field generator or irregularity in assemblage of the sensor group. More particularly, in the absence of the material to be examined, outputs of the phase detectors 76a, 76b, . . . should ideally be zero. But actually, there occur distorted wave outputs due to the irregularity described above. Specifically, the sensors are not uniform and the sinusoidal waves of the same period as that of the rotating magnetic field outputted from the low-pass filters 77a, 77b . . . have different peak values. Accordingly, these sinusoidal waves are sampled to generate irregular signals leading to noises. These signals having different peak values for the individual coils are cancelled out by means of the differential amplifiers 86a, 86b, . . . and cancellation voltage generators 85a, 85b, . . . . The cancellation voltage generator 85a, 85b, . . . generate a sine wave which is of the same period as that of the rotating magnetic field and of variable amplitude and phase, the amplitude and phase of the sine wave being made coincident with those of the outputs delivered out of the filters 77a, 77b, . . . in the absence of the examinee material to enable the sine wave to be cancelled out by means of the differential amplifiers 86a, 86b, . . . The amplitude and phase can be adjusted manually or automatically.

Figure 9:
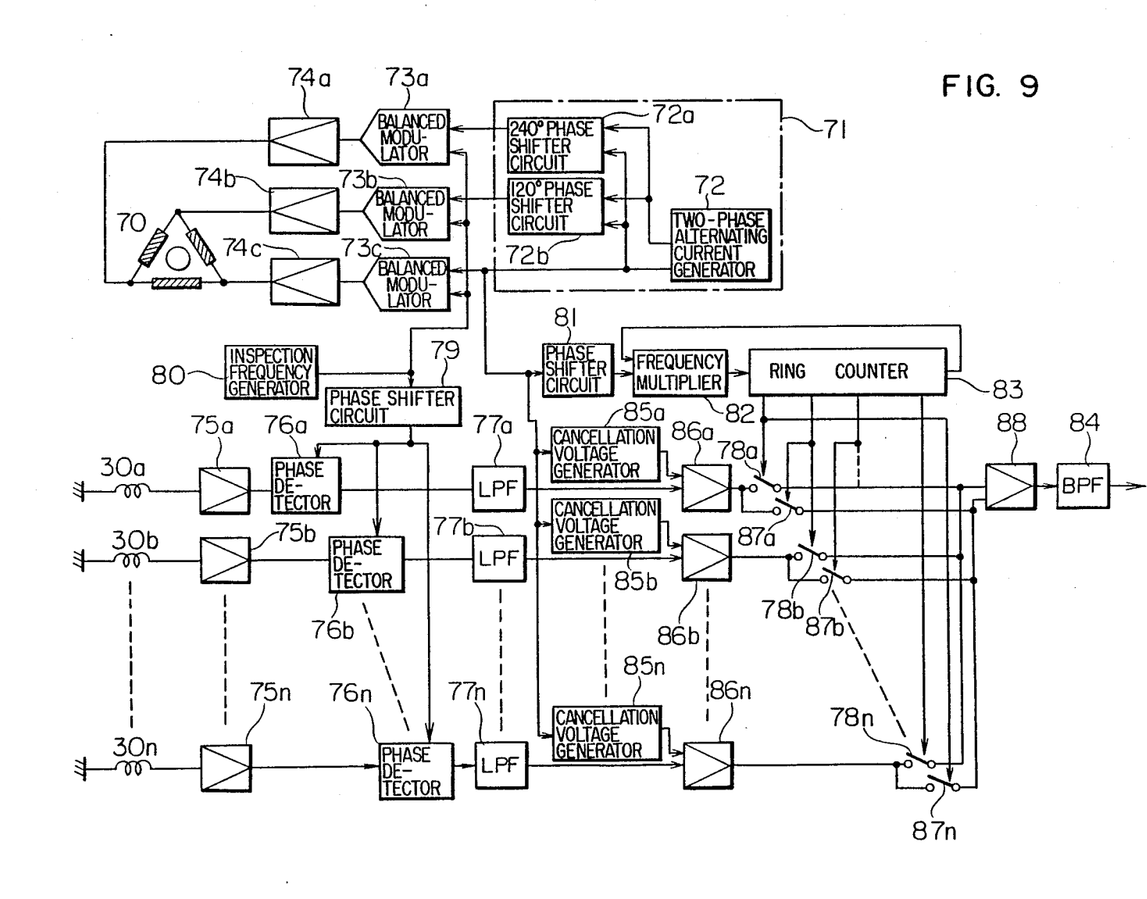

FIG. 9 shows an improvement on FIG. 8 capable of cancelling noises due to vibrations of the examinee material. Electronic switches 87a, 87b, . . . connected to the outputs of the differential amplifiers 86a, 86b, . . . , respectively, and a differential amplifier 88 constitute a means for this purpose, the switches 87a, 87b, . . . being controlled by the outputs of the ring counter 83 which are displaced by one from those for the switches 78a, 78b, . . . . More particularly, the same output turns on the switches 87a and 78b, the same output turns on the switches 87b and 78c, . . . and the same output turns on the switches 87n and 78n. The difference between outputs of the switches 78a, 78b, . . . and outputs of the switches 87a, 87b, . . . is determined by the amplifier 88 and applied to the band-pass filter 84.

Figure 12A:
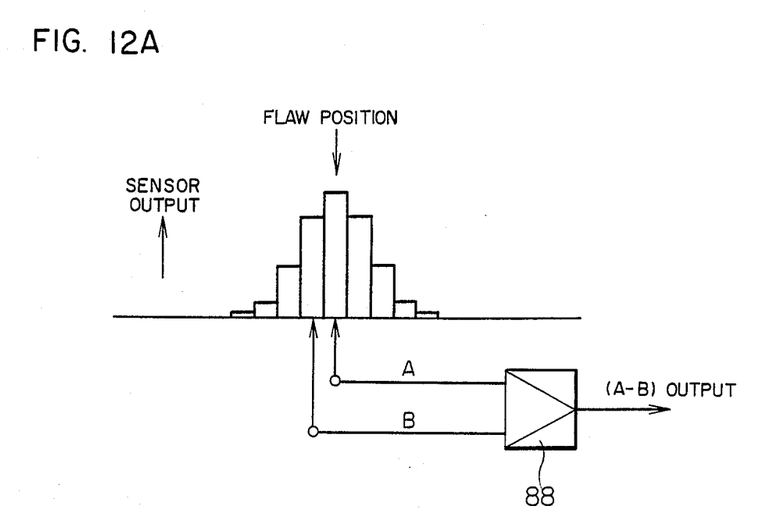
FIG. 12A and FIG. 12B are diagrams showing the relation between sensor output and flaw position in the case of absence of a circuit for cancelling out noises due to vibrations of a material to be examined and in the case of presence of the noise cancellation circuit.
Figure 12B:
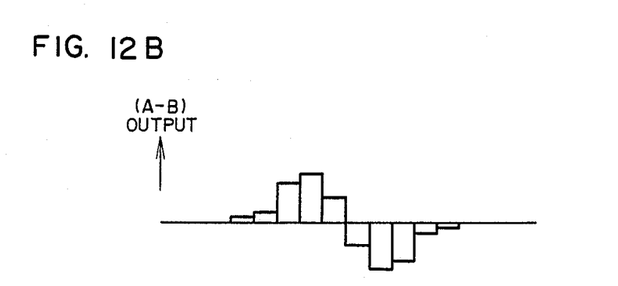

In comparison with FIG. 8, the output from differential amplifier 88 of FIG. 9 will be described with reference to FIGS. 12A and 12B. The sensor outputs are as shown at a bar graph in FIG. 12A and these outputs are applied to the recorder in the case of FIG. 8. Since the differential amplifier 88 sequentially determines the difference between the two adjacent outputs A and B, (A - B) outputs are obtained as shown in FIG. 12B. Considering that changes in coil outputs due to a vibration of the examinee material develop in adjacent two coils (in this example, 120 coils are arranged per circumference and the coil spacing is 3°) in the same amount, the changes are cancelled out through the above difference operation and a zero-cross point in the (A - B) outputs is considered to be representative of a flaw position.

For generation of the rotating magnetic field, use is not to be limited to the three-phase alternating current, as arbitrary m coils may be arranged with $2\pi/m$ displacement to generate an m-phase alternating current for excitation. The present invention may also use such a multiphase alternating current system.

INDUSTRIAL CAPABILITY

In the present invention, since a rotating magnetic field generated by a low frequency multiphase alternating current and a high frequency alternating current at an inspection frequency is superimposed on the rotating magnetic field so that a surface flaw of a material to be examined may be detected by using an electromagnetic effect induced in the examinee material by the high frequency alternating current, optimum values of the revolution number of the rotating magnetic field and the inspection frequency can be selected independently of each other in accordance with a material of the examinee material, position and size of a flaw to be detected, thereby providing method and apparatus for non-destructive inspection of metal matrials which can detect a surface flaw of a metal material with high efficiency and high sensitivity.

We claim:

1. An apparatus for non-destructive inspection of flaws in metal materials in which an electromagnetic effect is induced in the surface of an elongated metal material and a change in the electromagnetic effect depenent on the presence or absence of a surface flaw of the metal material is utilized, said apparatus comprising:

means for generating a rotating magnetic field formed as a hollow cylinder into which a material to be examined is insertable longitudinally thereof and having a multiphase winding arranged for generation of the rotating magnetic field;

a transmitting circuit for generating a low frequency multiphase alternating current at a frequency selected as to obtain the rotating magnetic field of a desired revolution number and having respective phases which are independently balancemodulated with a high frequency alternating current of an inspection frequency suitable for inducing said electromagnetic effect in the surface of the examinee material, said transmitting circuit being connected to apply said low frequency multiphase alternating current to said multiphase winding of said rotating magnetic field generating means;

a plurality of detecting elements arranged in the circumferential direction along the inner circumferential surface of said hollow cylindrical rotating magnetic field generating means and suitable for detecting a change in said electromagntic effect generated in the surface of the examinee material, said electromagnetic effect being an eddy current generated in the surface of the examinee material; and processing means, connected to output ends of said detecting elements, for processing an output from each detecting element to derive a signal indicative of the presence of a flaw at the surface of the examinee material; wherein said processing means includes:
(a) a plurality of phase detectors for phase-detecting the outputs of said detecting elements by using said high frequency alternating current of said inspection frequency as a reference wave;
(b) a plurality of low-pass filters for deriving, from respective outputs of said phase detectors, components having the same frequency as that of said low frequency multiphase alternating current; and
(c) a sampling circuit having a plurality of switches for sequentially sampling outputs of said plurality of low-pass filters in synchronism with the rotation of said rotating magnetic field.

2. An apparatus for non-destructive inspection of flaws in metal materials according to claim 1, further comprising:
a plurality of cancellation circuits outputs of said low-pass filters which develop when the examinee material has no flaw.

3. An apparatus for non-destructive inspection of flaws in metal materials according to claim 1, wherein said sampling circuit comprises:
two switch groups for sequntially sampling the outputs of said low-pass filters in synchronism with the rotation of said rotating magnetic field, operation timings for respective switch groups being controlled such that outputs of adjacent two detecting elements are sampled simultaneously by said two switch groups, respectively; and
a differential amplifier for determining the difference between two outputs sampled simultaneously.

4. An apparatus for non-destructive inspection of flaws in metal materials according to claim 1, further comprising:
a band-pass filter connected to the outputs of said sampling circuit to eliminate components other than the flaw information from the outputs of said sampling circuit.

5. An apparatus for non-destructive inspection of flaws in metal materials in which an electromagnetic effect is induced in the surface of an elongated metal material and a change in the electromagnetic effect dependent on the presence or absence of a surface flaw of the metal material is utilized, said apparatus comprising:
means for generating a rotating magnetic field formed as a hollow cylinder into which a material to be examined is insertable longitudinally thereof and having a multiphase winding arranged for generation of the rotating magnetic field;
a transmitting circuit for generating a low frequency multiphase alternating current at a frequency selected as to obtain the rotating magnetic field of a desired revolution number and having respective phases which are independently balancemodulated with a high frequency alternating current of an inspection frequency suitable for inducing said electromagnetic effect in the surface of the examinee material, said transmitting circuit being connected to apply said low frequency multiphase alternating current to said multiphase winding of said rotating magnetic field generating means;
a plurality of detecting elements arranged in the circumferential direction along the inner circumferential surface of said hollow cylindrical rotating magnetic field generating means and suitable for detecting a change n said electromagnetic effect generated in the surface of the examinee material, said electromagnetic effect being leakage magnetic flux generated in the surface of the examinee material; and
processing means, connected to output ends of said detecting element, for processing an output from each detecting element to derive a signal indicative of the presence of a flaw at the surface of the examinee material; wherein said processing means includes:
(a) a plurality of phase detectors for phase-detecting the outputs of said detecting elements by using said high frequency alternating current of said inspection frequency as a reference wave;
(b) a plurality of low-pass filters for deriving, from respective outputs of said phase detectors, components having the same frequency as that of said low frequency multiphase alternating current; and
(c) a sampling circuit having a plurality of switches for sequentially sampling outputs of said plurality of low-pass filters in synchronism with the rotation of said rotating magnetic field.

6. An apparatus for non-destructive inspection of flaws in metal materials according to claim 5, further comprising:
a plurality of cancellation circuits provided between said low-pass filters and said switches, for cancelling out outputs of said low-pass filters which develop when the examinee material has no flaw.

7. An apparatus for non-destructive inspection of flaws in metal materials according to claim 5, wherein said sampling circuit comprises:
two switch groups for sequentially sampling the outputs of said low-pass filters in synchronism with the rotation of said rotating magnetic field, operation timings for the respective switch groups being controlled such that outputs of ajacent two detecting elements are sampled simultaneously by said two switch groups, respectively; and
a differential amplifier for determining the difference between two outputs sampled simultaneously.

8. An apparatus for non-destructive inspection of flaws in metal materials according to claim 5, further comprising:
a band-pass filter connected to the outputs of said sampling circuit to eliminate components other than the flaw information from the outputs of said sampling circuits.

* * * * *